US012648744B2

(12) United States Patent
Pyeon

(10) Patent No.: US 12,648,744 B2
(45) Date of Patent: Jun. 9, 2026

(54) RADIATION PROTECTION DEVICE AND RADIOGRAPHIC IMAGING APPARATUS INCLUDING THE SAME

(71) Applicant: Vieworks Co., Ltd., Anyang-si (KR)

(72) Inventor: Yeong Hyeon Pyeon, Anyang-si (KR)

(73) Assignee: Vieworks Co., Ltd., Anyang-si (KR)

( * ) Notice: Subject to any disclaimer, the term of this patent is extended or adjusted under 35 U.S.C. 154(b) by 461 days.

(21) Appl. No.: 18/345,561

(22) Filed: Jun. 30, 2023

(65) Prior Publication Data

US 2024/0050049 A1    Feb. 15, 2024

(30) Foreign Application Priority Data

Aug. 10, 2022    (KR) ........................ 10-2022-0099966

(51) Int. Cl.
A61B 6/10          (2006.01)
A61B 6/50          (2024.01)

(52) U.S. Cl.
CPC .............. A61B 6/107 (2013.01); A61B 6/502 (2013.01)

(58) Field of Classification Search
CPC ........... A61B 6/107; A61B 6/44; A61B 6/502; A61B 6/10; A61G 11/005
See application file for complete search history.

(56) References Cited

U.S. PATENT DOCUMENTS

| | | | | |
|---|---|---|---|---|
| 4,158,779 A | * | 6/1979 | Rommel | ................. A61B 6/107 |
| | | | | 976/DIG. 335 |
| 4,923,162 A | * | 5/1990 | Fleming | ................. F16M 11/14 |
| | | | | 248/481 |
| 5,340,171 A | * | 8/1994 | Slaybuagh | ............ E05B 47/023 |
| | | | | 292/201 |
| 7,315,607 B2 | * | 1/2008 | Ramsauer | .............. A61B 6/502 |
| | | | | 378/37 |
| 7,792,245 B2 | * | 9/2010 | Hitzke | ................... A61B 6/107 |
| | | | | 378/37 |
| 9,420,982 B2 | * | 8/2016 | Kim | ........................ A61B 6/502 |
| D772,414 S | * | 11/2016 | Ballsieper | .................... D24/158 |
| 9,877,688 B1 | * | 1/2018 | Colling | ................... A61B 6/107 |
| 10,136,871 B2 | * | 11/2018 | Yorkston | .............. A61B 6/4452 |

(Continued)

FOREIGN PATENT DOCUMENTS

| | | |
|---|---|---|
| DE | 10 2006 044483 A1 | 5/2007 |
| KR | 20-0490677 Y1 | 12/2019 |

OTHER PUBLICATIONS

Ivan Ordavo, "Extended European Search Report for EP Application No. 23182132.3", Dec. 21, 2023, EPO, DE.

*Primary Examiner* — Wyatt A Stoffa
(74) *Attorney, Agent, or Firm* — Bridgeway IP Law Group, PLLC; Jihun Kim

(57)          ABSTRACT

Disclosed is a radiation protection device provided for a radiographic imaging apparatus to shield radiation from being irradiated to a body side of a patient other than an imaging target, and a radiographic imaging apparatus including the same. The radiation protection device includes a fixing unit fixed to an arm unit of a radiographic imaging apparatus; an elevation unit coupled to the fixing unit to be movable along a first direction; a connecting unit coupled to the elevation unit to be rotatable in a second direction different from the first direction; and a shielding unit provided on one side of the connecting unit to shield radiation, and a radiographic imaging apparatus including the radiation protection device.

18 Claims, 13 Drawing Sheets

(56) References Cited

U.S. PATENT DOCUMENTS

| | | | | |
|---|---|---|---|---|
| 10,722,186 B2 * | 7/2020 | Nishi | A61B 6/4476 | |
| 11,617,548 B2 * | 4/2023 | DeFreitas | A61B 6/4417 | |
| | | | 378/20 | |
| 12,144,668 B2 * | 11/2024 | Smith | A61B 6/482 | |
| 12,268,535 B2 * | 4/2025 | Wells | A61B 6/0492 | |
| 12,295,764 B2 * | 5/2025 | Hisata | A61B 6/462 | |
| 2007/0138415 A1 * | 6/2007 | Rees | A61B 6/107 | |
| | | | 250/516.1 | |
| 2009/0032892 A1 * | 2/2009 | Hsiao | H10F 39/016 | |
| | | | 257/431 | |
| 2009/0052616 A1 * | 2/2009 | Honjo | A61B 6/032 | |
| | | | 378/189 | |
| 2009/0220055 A1 * | 9/2009 | Nakata | A61B 6/107 | |
| | | | 378/208 | |
| 2009/0323892 A1 * | 12/2009 | Hitzke | A61B 6/502 | |
| | | | 378/37 | |
| 2010/0183119 A1 * | 7/2010 | Ludwig | A61B 6/025 | |
| | | | 378/37 | |
| 2013/0270462 A1 * | 10/2013 | Beck | F16M 11/42 | |
| | | | 250/516.1 | |
| 2013/0320246 A1 * | 12/2013 | Beck | A61B 6/4423 | |
| | | | 250/515.1 | |
| 2013/0331682 A1 * | 12/2013 | Ohta | A61B 6/022 | |
| | | | 600/407 | |
| 2014/0205060 A1 * | 7/2014 | Kim | A61B 6/502 | |
| | | | 378/20 | |
| 2014/0264094 A1 * | 9/2014 | Heller | G21F 3/00 | |
| | | | 250/515.1 | |
| 2015/0025377 A1 * | 1/2015 | Nishi | A61B 6/025 | |
| | | | 600/436 | |
| 2015/0141799 A1 * | 5/2015 | Rapoport | A61B 5/055 | |
| | | | 600/410 | |
| 2016/0220199 A1 * | 8/2016 | Gordon | A61B 6/107 | |
| 2019/0137418 A1 * | 5/2019 | Price | G01N 23/02 | |
| 2020/0168353 A1 * | 5/2020 | Goldstein | G21F 1/125 | |
| 2024/0188908 A1 * | 6/2024 | DeFreitas | A61B 6/0414 | |
| 2025/0032069 A1 * | 1/2025 | Foster | A61B 6/107 | |
| 2025/0228511 A1 * | 7/2025 | Robinson | A61B 6/46 | |
| 2025/0262005 A1 * | 8/2025 | Ruff | A61B 90/98 | |

* cited by examiner (a)

(b)

(a)

(b)

57

56

1

RADIATION PROTECTION DEVICE AND RADIOGRAPHIC IMAGING APPARATUS INCLUDING THE SAME

CROSS-REFERENCE TO RELATED APPLICATIONS

This application claims priority to and the benefit of Korean Patent Application No. 10-2022-0099966 filed in the Korean Intellectual Property Office on Aug. 10, 2022, the entire contents of which are incorporated herein by reference.

TECHNICAL FIELD

The present invention relates to a radiation protection device provided for a radiographic imaging apparatus to shield radiation from being irradiated to a body side of a patient other than an imaging target, and a radiographic imaging apparatus including the same.

BACKGROUND ART

In the medical field, a radiographic imaging apparatus for diagnosing diseases are used in various manners. For example, mammography, which refers to a radiographic breast imaging technology for imaging a breast by using radiation such as X-ray, has not only various advantages of radiography but also a unique feature of minimizing the exposure by enlarging an image, reducing the number of imaging, increasing the resolution, and adjusting the brightness and contrast ratio, as a result of which the use of the mammography is rapidly spreading.

The mammography apparatus may include a column arranged perpendicular to a floor and having a columnar shape, a C-arm having a C shape or a shape similar thereto as a whole by being bent in an arc shape so that two opposite ends thereof face each other in a state in which a middle part is connected to the column so as to be movable upward and downward and rotatable along the column, a radiation generator that is mounted at one end of the C-arm and emits radiation toward the other end facing the one end, a detector arranged to face the radiation generator, and a compressing unit (also referred to as a 'compression paddle') for compressing a breast.

During the mammography using the radiation, it is desirable not only to minimize a radiation dose to the breast, but also to block radiation to a human body other than an imaging target.

U.S. Pat. No. 7,792,245 discloses an X-ray system having a face shield that blocks radiation from being irradiated to a patient's face during X-ray imaging of the patient's breast.

However, according to the technology of the related art, there are disadvantages in that it is difficult to shield radiation adaptively according to a radiographic imaging method and a patient's body condition and it is difficult to secure a working space for adjusting a compression part or the like.

SUMMARY OF THE INVENTION

The present invention has been made in an effort to provide a radiation protection device that can be easily adjusted according to a radiographic imaging condition or a patient's body condition to shield radiation from being irradiated toward a patient's body other than an imaging target, and a radiographic imaging apparatus including the same.

Exemplary embodiments of the present invention provide a radiation protection device including a fixing unit fixed to an arm unit of a radiographic imaging apparatus; an elevation unit coupled to the fixing unit to be movable along a first direction; a connecting unit coupled to the elevation unit to be rotatable in a second direction different from the first direction; and a shielding unit provided on one side of the connecting unit to shield radiation, and a radiographic imaging apparatus including the radiation protection device.

In an exemplary embodiment, the fixing unit may include a fixing pin and a fixing hook protruding from a rear surface of the fixing unit, and the fixing hook may be configured to fix the fixing unit to the arm unit by being hooked on an engaging part provided inside the arm unit.

The fixing unit may include a disengaging operation part configured to rotate the fixing hook for releasing an engaged state of the fixing hook.

In an exemplary embodiment, the elevation unit may include a guide part fixed to the fixing unit, a movable block configured to be movable along the guide part, and a rotation support part provided on one side surface of the movable block and configured to rotatably support the connecting unit.

The guide part may have a plurality of position fixing holes formed at different heights along the first direction, and the movable block or the rotation support part may have a position fixing pin configured to be inserted into one of the position fixing holes for fixing a position.

The position fixing pin may be configured to be pressed toward the position fixing holes by a position fixing spring, and the elevation unit may further include an actuating lever for separating the position fixing pin from the position fixing hole.

The elevation unit may further include a static load spring for supporting the movable block from an upper side.

A rotation part of the connecting unit rotatably coupled to the rotation support part may be formed with a slot, and an actuation of the actuating lever may be allowed only in a state in which the slot is aligned with the actuating lever.

In an exemplary embodiment, the connecting unit may include a connecting unit frame, a rotation part provided on one side of the connecting unit frame and coupled to the rotation support part of the elevation unit, and a rotation fixing part provided on the connecting unit frame and configured to selectively enable rotation of the rotation part with respect to the rotation support part.

The rotation support part may be provided with a fixing shaft having a fixing groove formed on an outer circumferential surface thereof, the rotation part may be coupled to the rotation support part by using the fixing shaft as a rotation axis, and the rotation fixing part may include a rotation fixing pin configured to block rotation of the rotation part by being inserted into the fixing groove.

The rotation fixing pin may be configured to be pressed toward the fixing groove by a rotation fixing spring, and the connecting unit may include an unfixing operation part configured to be operated to separate the rotation fixing pin from the fixing groove.

The connecting unit frame may be provided with a rotation fixing pin driving link configured to retract the rotation fixing pin by an operation of the unfixing operation part.

In an exemplary embodiment, rotation of the connecting unit with respect to the elevation unit may be allowed when the elevation unit is positioned at a predetermined height in the first direction.

The rotation part of the connecting unit may be provided with a slot, and the radiation protection device may further include a locking piece configured to prevent rotation of the connecting unit in the second direction by being partially inserted into the slot, and to release an inserted state into the slot by a locking piece release part at the predetermined height.

According to exemplary embodiments of the present invention, when performing the radiographic imaging operation, it is possible to effectively shield radiation from being irradiated toward a patient's body other than an imaging target, and to improve the convenience of the radiographic imaging operation.

For example, the radiation protection device according to the exemplary embodiment of the present invention is configured to be adjustable in height in the vertical direction, and therefore, can be easily adjusted according to a radiographic imaging condition or a patient's body condition, thereby improving the effect of shielding radiation from being irradiated to the patient's body.

The radiation protection device according to the exemplary embodiment of the present invention is configured to be rotatable in the left-right direction, so that an operation space can be secured during radiographic imaging, thereby improving the convenience of the radiographic imaging operation.

The foregoing summary is illustrative only and is not intended to be in any way limiting. In addition to the illustrative aspects, embodiments, and features described above, further aspects, embodiments, and features will become apparent by reference to the drawings and the following detailed description.

Figure 1:
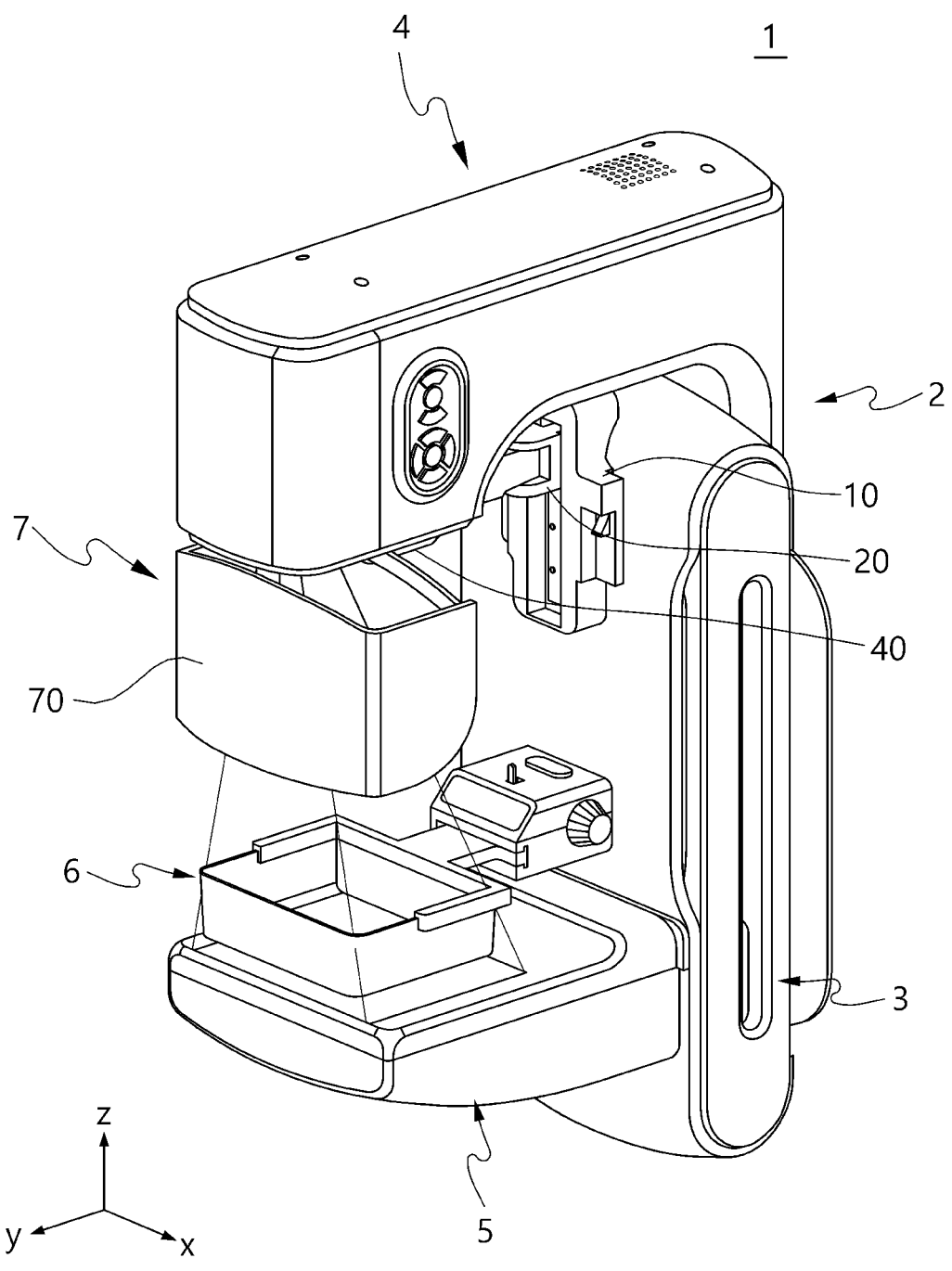
FIG. 1 is a perspective view showing a radiographic imaging apparatus including a radiation protection device according to an exemplary embodiment of the present invention.
Figure 2:
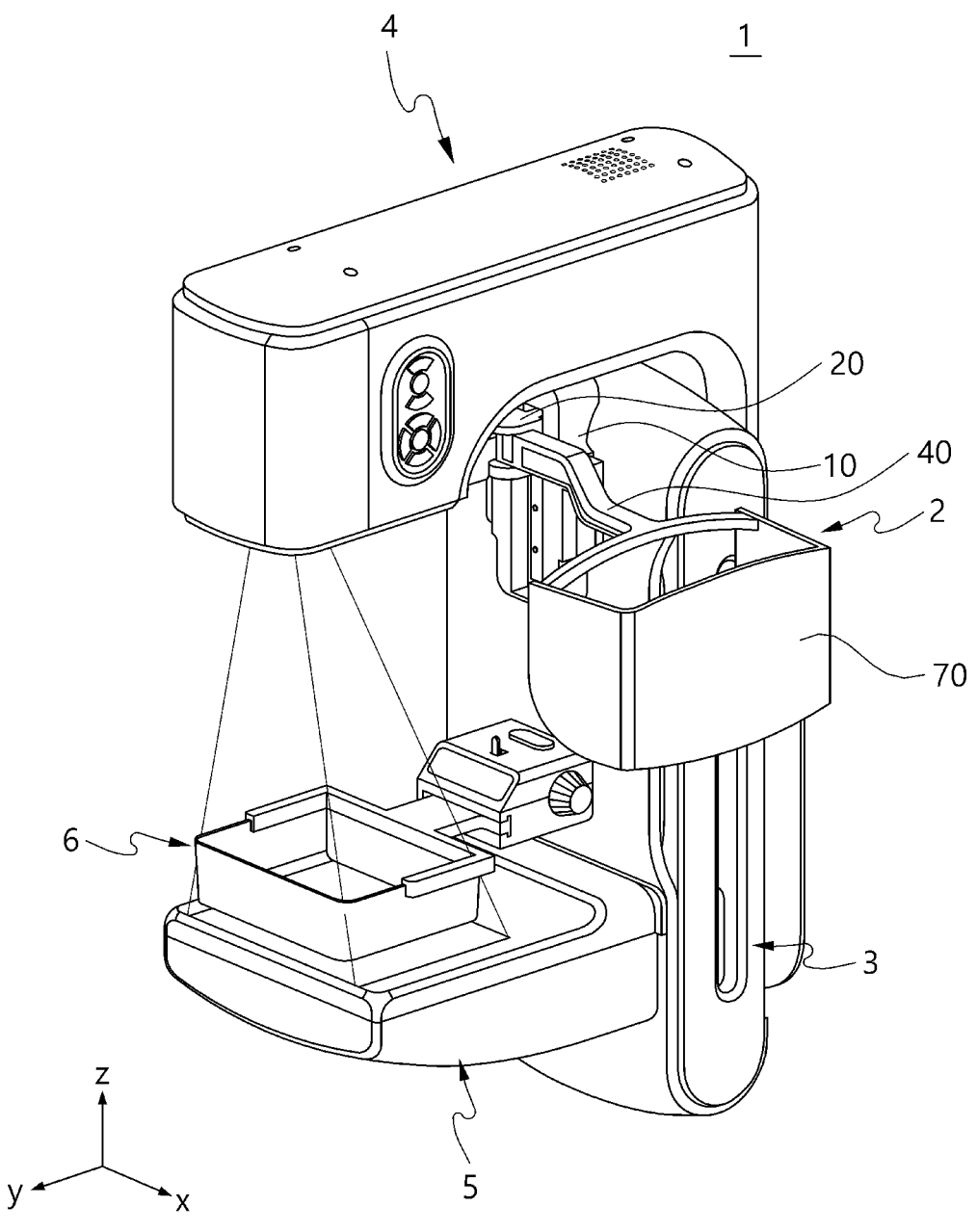
FIG. 2 is a perspective view showing a state in which a shielding unit of the radiation protection device is rotated in the radiographic imaging apparatus including the radiation protection device according to the exemplary embodiment of the present invention.
Figure 10:
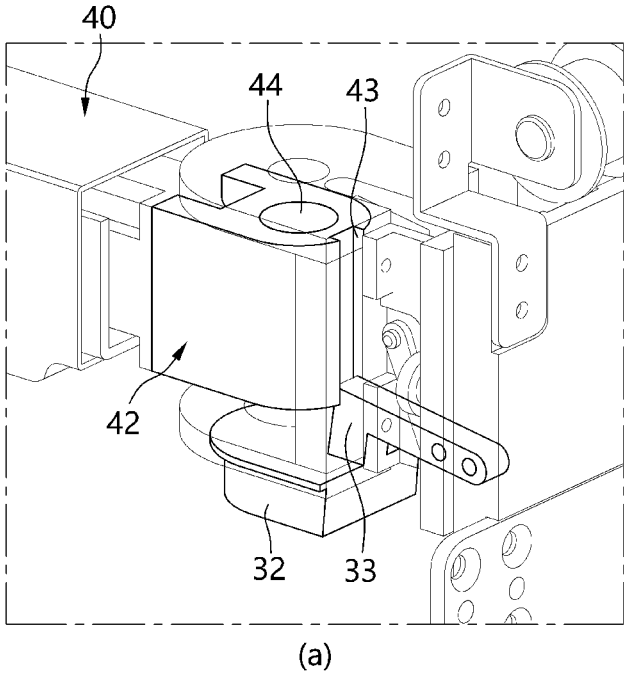
Figure 10:
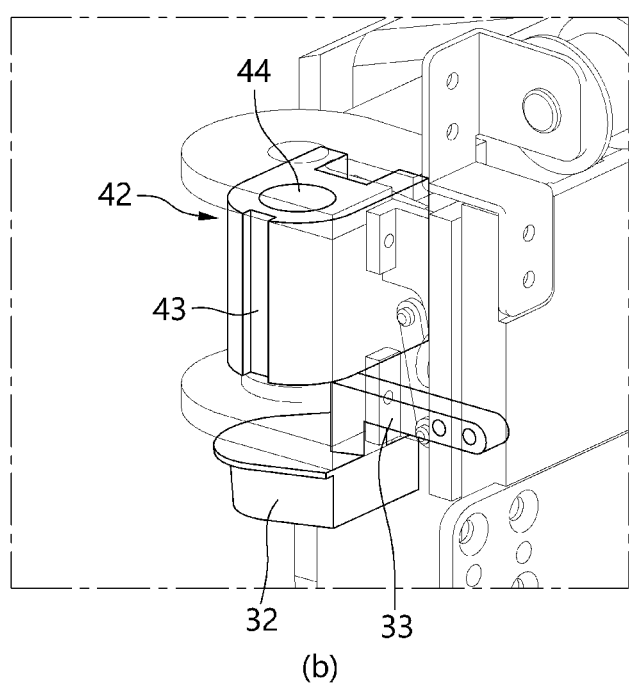

Part (a) of FIG. 10 is a view showing a rotation part provided for a connecting unit of the radiation protection device and an actuating lever of the elevation unit in a state of FIG. 1, and part (b) of FIG. 10 is a view showing the rotation part provided for the connecting unit of the radiation protection device and the actuating lever of the elevation unit in a state of FIG. 2.

Figure 11:
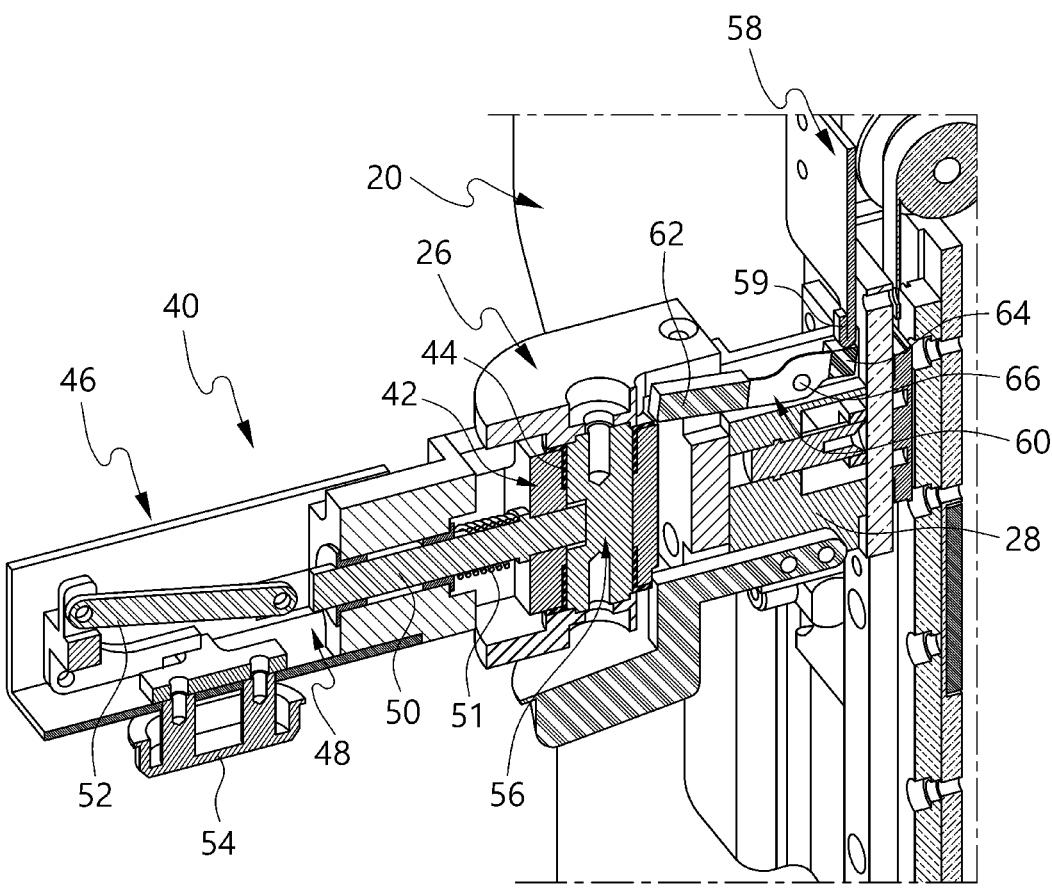

FIG. 11 is a cross-sectional view showing a detailed configuration of the connecting unit connected to a rotation support part of the radiation protection device according to the exemplary embodiment of the present invention.

Figure 12:
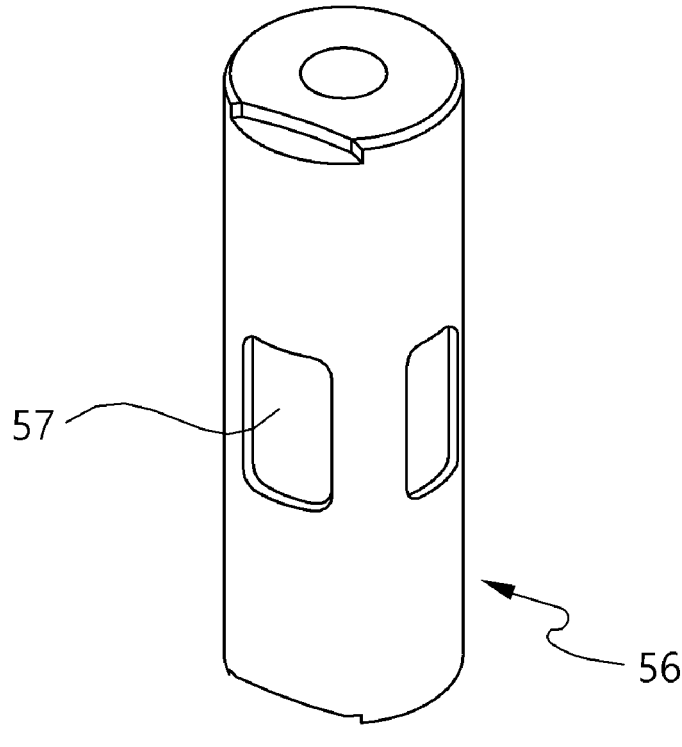

FIG. 12 is a perspective view of a fixing shaft provided for the rotation support part of the radiation protection device according to the exemplary embodiment of the present invention.

Figure 13:
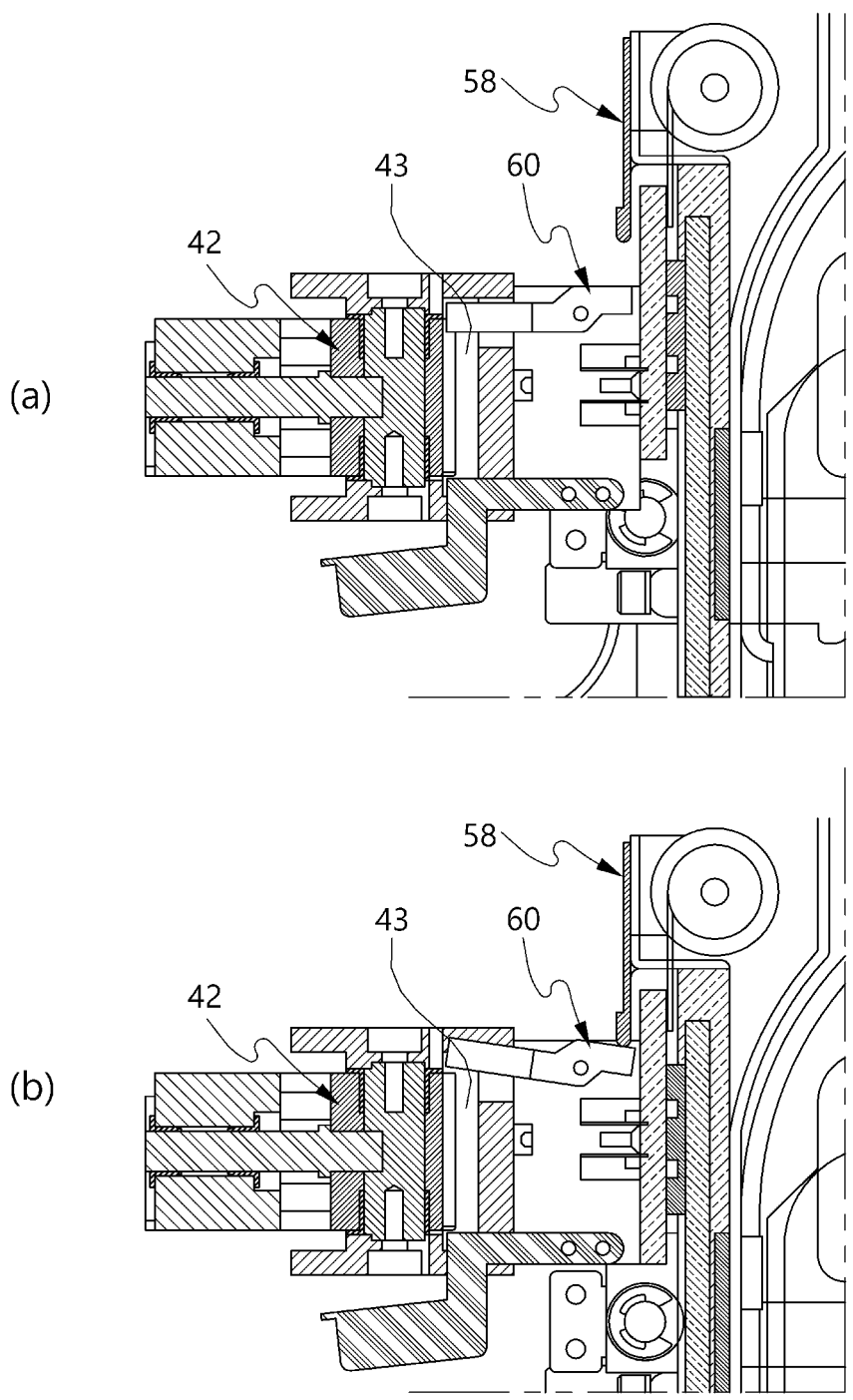

FIG. 13 is a view showing a height at which rotation of the connecting unit of the radiation protection device according to the exemplary embodiment of the present invention can be enabled.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, exemplary embodiments of the present invention will be described in detail with reference to the accompanying drawings. First, when adding reference numerals to components in each drawing, it should be noted that the same components have the same numerals as much as possible even if they are shown in different drawings. In addition, when describing the present invention, a detailed description of related known configurations or functions will be omitted if it is determined that the detailed description makes the gist of the present invention unclear. Further, although preferred embodiments of the present invention will be described below, the technical idea of the present invention is not limited thereto and can be modified and implemented in various ways by one skilled in the art.

Figure 3:
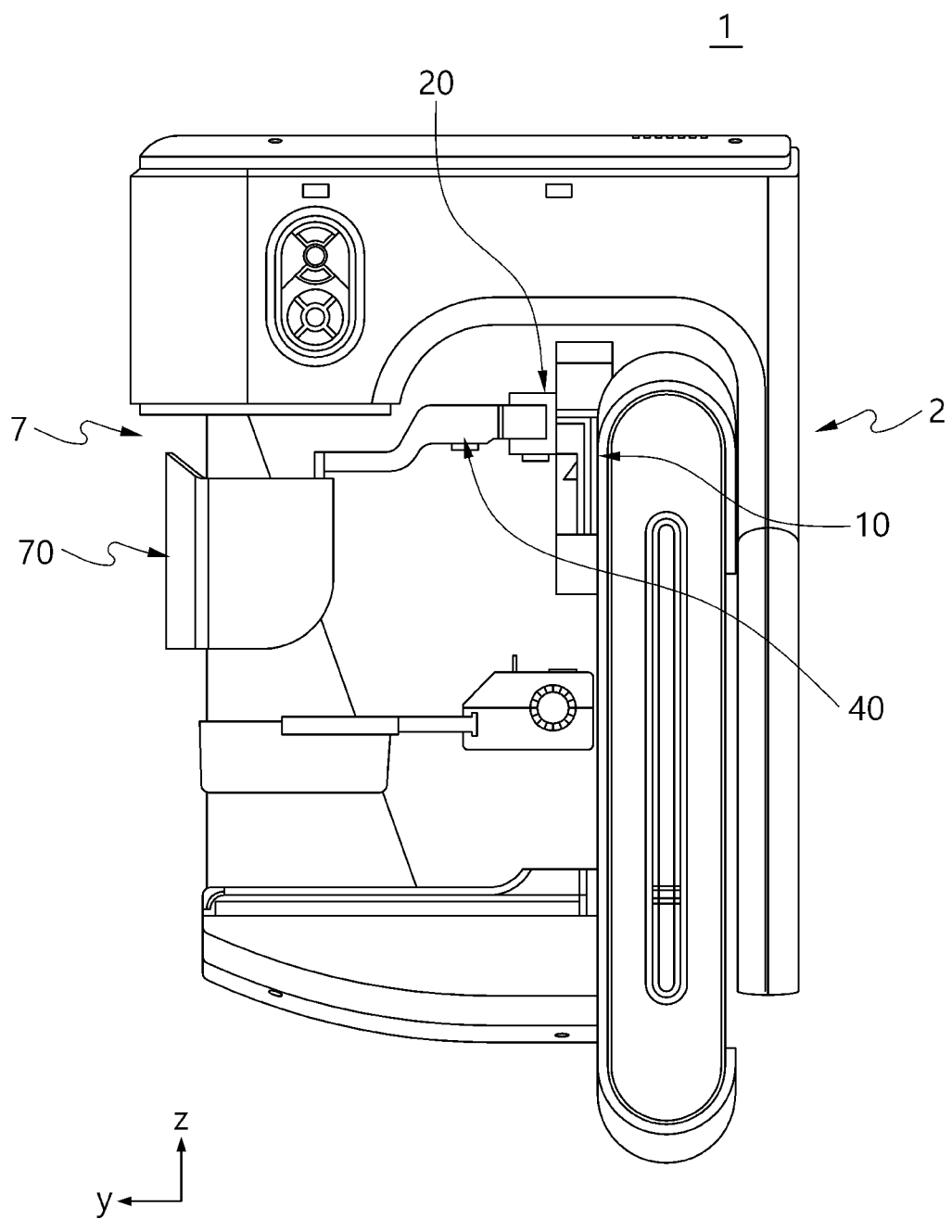
FIG. 3 is a side view showing the radiographic imaging apparatus including the radiation protection device according to the exemplary embodiment of the present invention.
Figure 4:
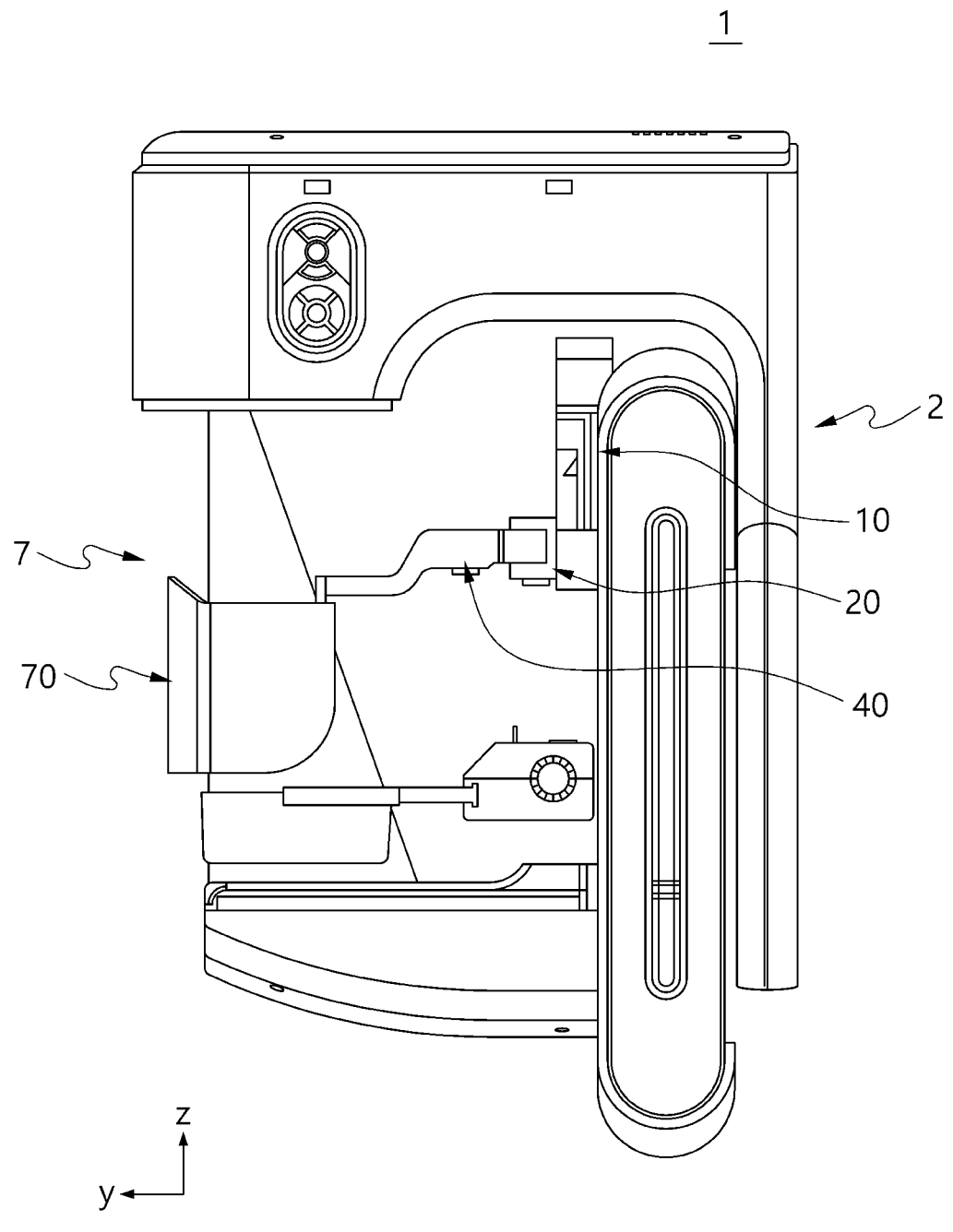
FIG. 4 is a side view showing a state in which the shielding unit of the radiation protection device is moved down in the radiographic imaging apparatus including the radiation protection device according to the exemplary embodiment.

FIG. 1 is a perspective view showing a radiographic imaging apparatus including a radiation protection device according to an exemplary embodiment of the present invention, and FIG. 2 is a perspective view showing a state in which a shielding unit of the radiation protection device is rotated in the radiographic imaging apparatus including the radiation protection device according to the exemplary embodiment of the present invention. FIG. 3 is a side view showing the radiographic imaging apparatus including the radiation protection device according to the exemplary embodiment of the present invention, and FIG. 4 is a side view showing a state in which the shielding unit of the radiation protection device is moved down in the radiographic imaging apparatus including the radiation protection device according to the exemplary embodiment.

A radiographic imaging apparatus 1 including a radiation protection device 7 according to an exemplary embodiment of the present invention includes a support stand placed on the ground (not shown), an arm unit 2 mounted on the support stand, and the radiation protection device 7 provided for the arm unit 2.

In an exemplary embodiment, the arm unit 2 may be configured in the form of a C-arm, and the arm unit 2 may be provided in the form of being rotatable about a y-axis direction with respect to the support stand provided along a z-axis direction.

The arm unit 2 may include a main body part 3, an upper arm 4 provided at an upper end of the main body part 3, and a lower arm 5 provided at a lower end of the main body part 3. The upper arm 4 may be provided with a radiation emitter for emitting radiation, and the lower arm 5 may be provided with a radiation detector for detecting radiation emitted from the radiation emitter. When the radiographic imaging apparatus 1 according to the present invention is a mammography apparatus, the arm unit 2 may further include a compression part 6 for compressing a breast placed on an upper surface of the lower arm 5 from above. The compression part 6 may be provided to the main body part 3 so as to be elevated in the z-axis direction.

In an exemplary embodiment, the radiation protection device 7 includes a fixing unit 10 fixed to the main body part 3, an elevation unit 20 coupled to the fixing unit 10 to be movable in the z-axis direction, a connecting unit 40 coupled to the elevation unit 20 to be rotatable leftward or rightward, and a shielding unit 70 provided on one side of the connecting unit 40.

Referring to FIG. 2, as the connecting unit 40 rotates rightward with respect to the elevation unit 20, the shielding unit 70 moves rightward, and accordingly, an operation space can be secured between the upper arm 4 and the lower arm 5.

Referring to FIG. 4, as the elevation unit 20 is moved down in the z-axis direction, the connecting unit 40 and the shielding unit 70 connected to the elevation unit 20 are moved down. By moving up or down the shielding unit 70 according to a patient's body condition or a radiographic imaging condition, the shielding unit 70 may be adjusted to be positioned at an appropriate height for radiation blocking.

Figure 5:
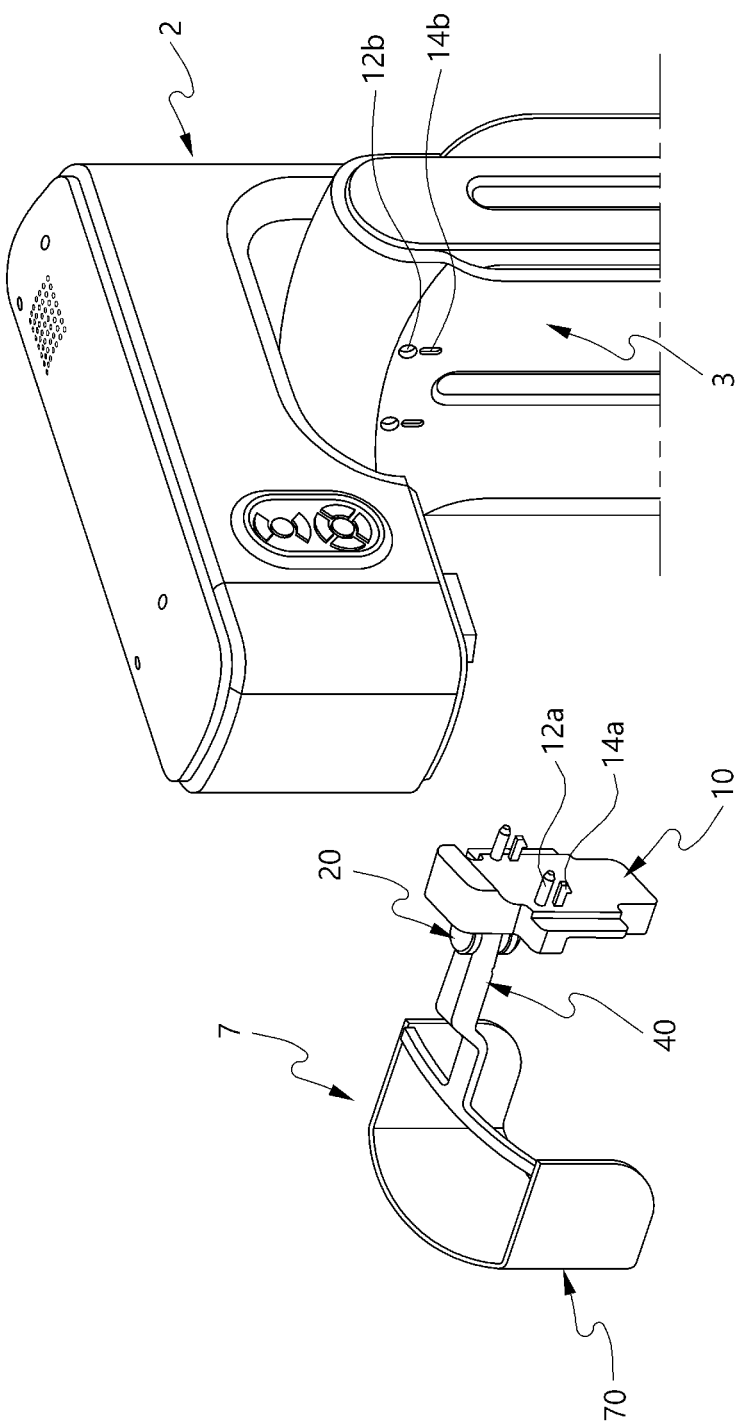
FIG. 5 is a perspective view showing a state in which the radiation protection device according to the exemplary embodiment of the present invention is separated from an arm unit.
Figure 6:
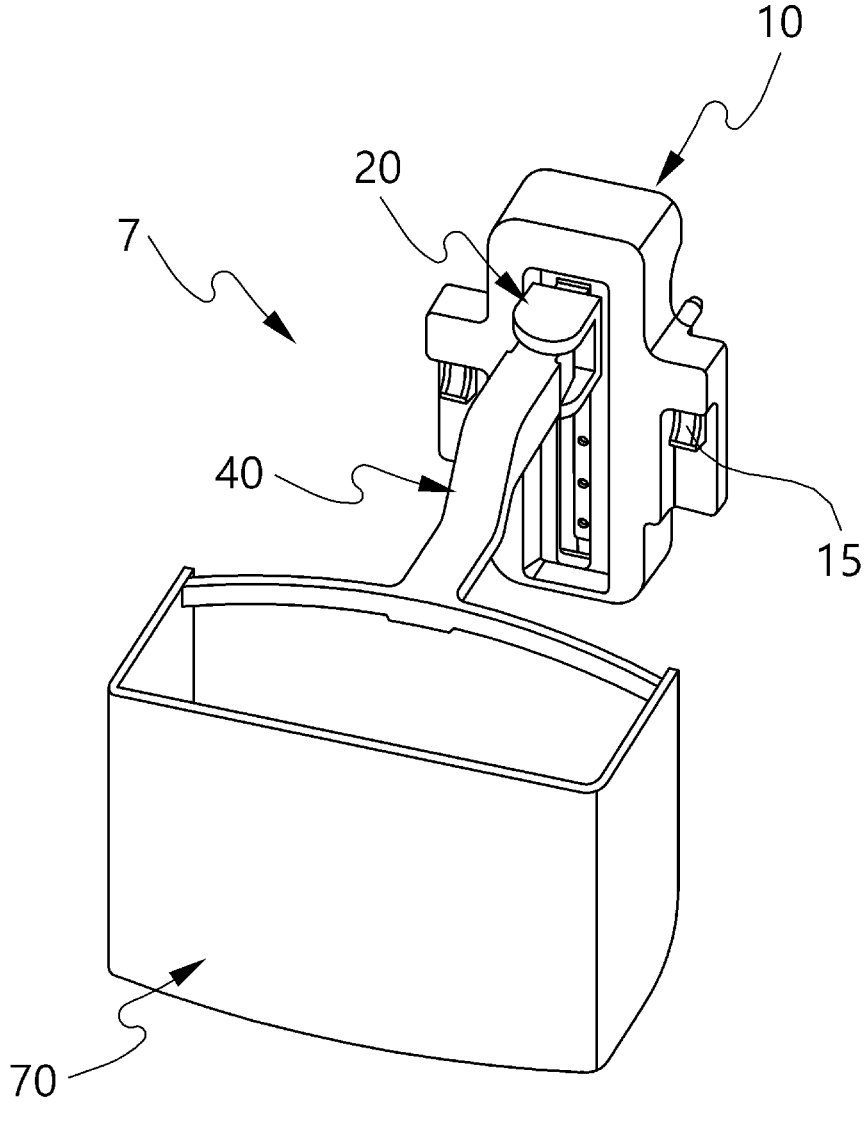
FIG. 6 is a perspective view of the radiation protection device according to the exemplary embodiment of the present invention.
Figure 7:
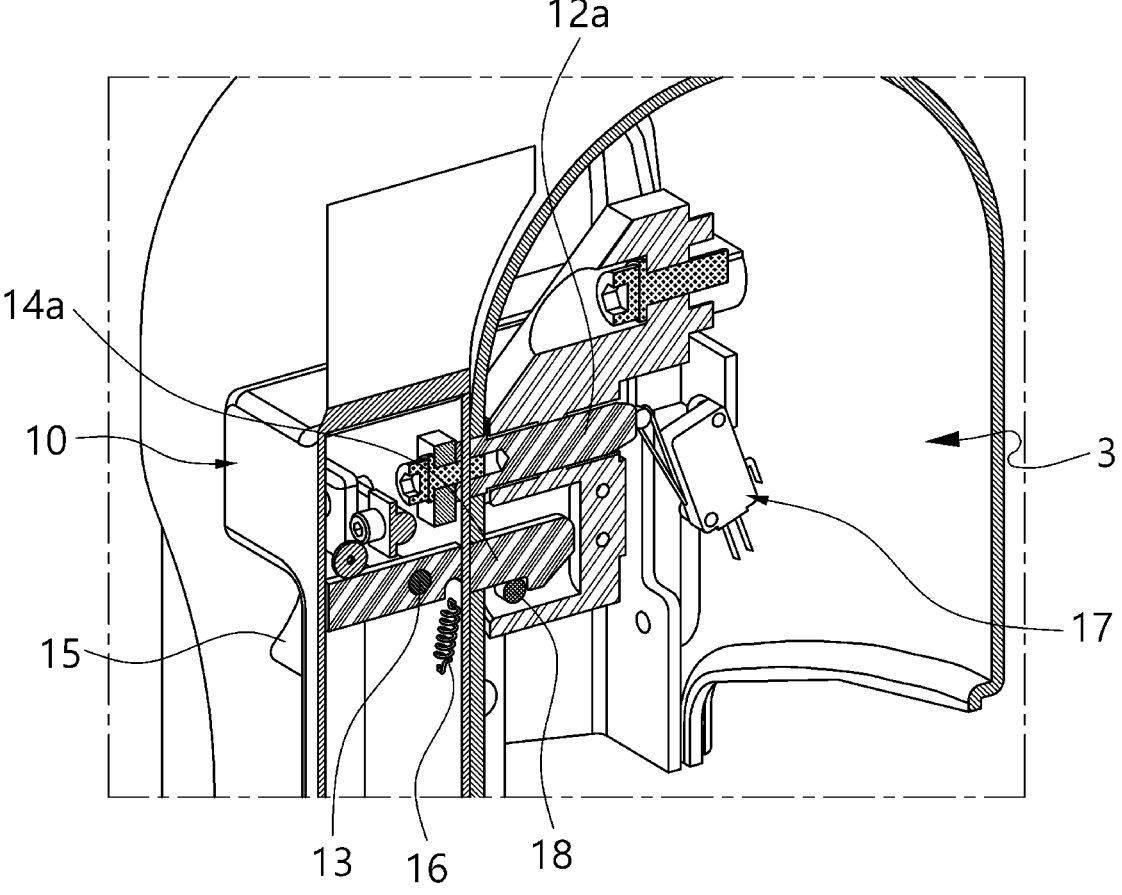
FIG. 7 is a cross-sectional view showing a configuration for fixing the radiation protection device according to the exemplary embodiment of the present invention to the arm unit.

FIG. 5 is a perspective view showing a state in which the radiation protection device according to the exemplary embodiment of the present invention is separated from an arm unit, FIG. 6 is a perspective view of the radiation protection device according to the exemplary embodiment of the present invention, and FIG. 7 is a cross-sectional view showing a configuration for fixing the radiation protection device according to the exemplary embodiment of the present invention to the arm unit.

The fixing unit 10 of the radiation protection device 7 is provided with a fixing element for fixing the fixing unit 10 to the main body part 3 of the arm unit 2. In an exemplary embodiment, the fixing element includes a fixing pin 12a and a fixing hook 14a protruding from a rear surface of the fixing unit 10. The main body part 3 is formed with a fixing pin insertion hole 12b into which the fixing pin 12a is inserted and a fixing hook insertion hole 14b into which the fixing hook 14a is inserted.

Referring to FIG. 7, the fixing pin 12a is inserted into the fixing pin insertion hole 12b, and an end portion of the fixing pin 12a may come into contact with a mounting detection switch 17 provided inside the main body part 3. When the fixing pin 12a contacts or presses the mounting detection switch 17, it can be determined by an electrical signal that the radiation protection device 7 is mounted to the arm unit 2.

A control unit (not shown) of the radiographic imaging apparatus 1 may adjust the maximum lifting height of the compression part 6 when it recognizes, based on the signal of the mounting detection switch 17, that the radiation protection device 7 is mounted. In an exemplary embodiment, the compression part 6 may be moved up and down by a separate drive motor provided in the main body part 3, and the control unit adjusts the maximum lifting height of the compression part 6 to prevent interference or collision with the radiation protection device 7. In addition, the control unit may provide a guide message for confirming a location of the shielding unit 70 before starting radiographic imaging.

Meanwhile, the fixing hook 14a inserted into the fixing hook insertion hole 14b is engaged with an engaging part 18 provided in the main body part 3, and therefore, can fix the fixing unit 10 to the main body part 3.

Referring to FIG. 6, a front surface of the fixing unit 10 may be provided with a disengaging operation part 15 capable of releasing an engaged state of the fixing hook 14a. When the disengaging operation part 15 is operated, the fixing hook 14a is moved, so that the engaged state with the engaging part 18 can be released. In an exemplary embodiment, the disengaging operation part 15 can be actuated so that an end portion of the fixing hook 14a on the main body part 3 side is moved upward. Referring to FIG. 7, the fixing hook 14a is coupled to a fixing hook rotation shaft 13 in the fixing unit 10, and is provided with a fixing hook spring 16 for pulling downward the end portion of the fixing hook 14a on the main body part 3 side. An end portion of the fixing hook 14a on an opposite side to the main body part 3 is connected to the disengaging operation part 15, and when the disengaging operation part 15 is pressed downward, the end portion of the fixing hook 14a on the main body part 3 side is moved up, so that the engaged state with the engaging part 18 is released.

In an implementation of the present invention, the fixing pin 12a may be screwed into the fixing pin insertion hole 12b. In this case, the fixing hook 14a may not be provided. However, as described above, when the fixing pin 12a is inserted into the fixing pin insertion hole 12b and the fixing unit 10 is fixed to the main body part 3 by the fixing hook 14a, the radiation protection device 7 can be quickly attached and detached with respect to the main body part 3.

Next, a configuration of the elevation unit 20 of the radiation protection device 7 will be described.

Figure 8:
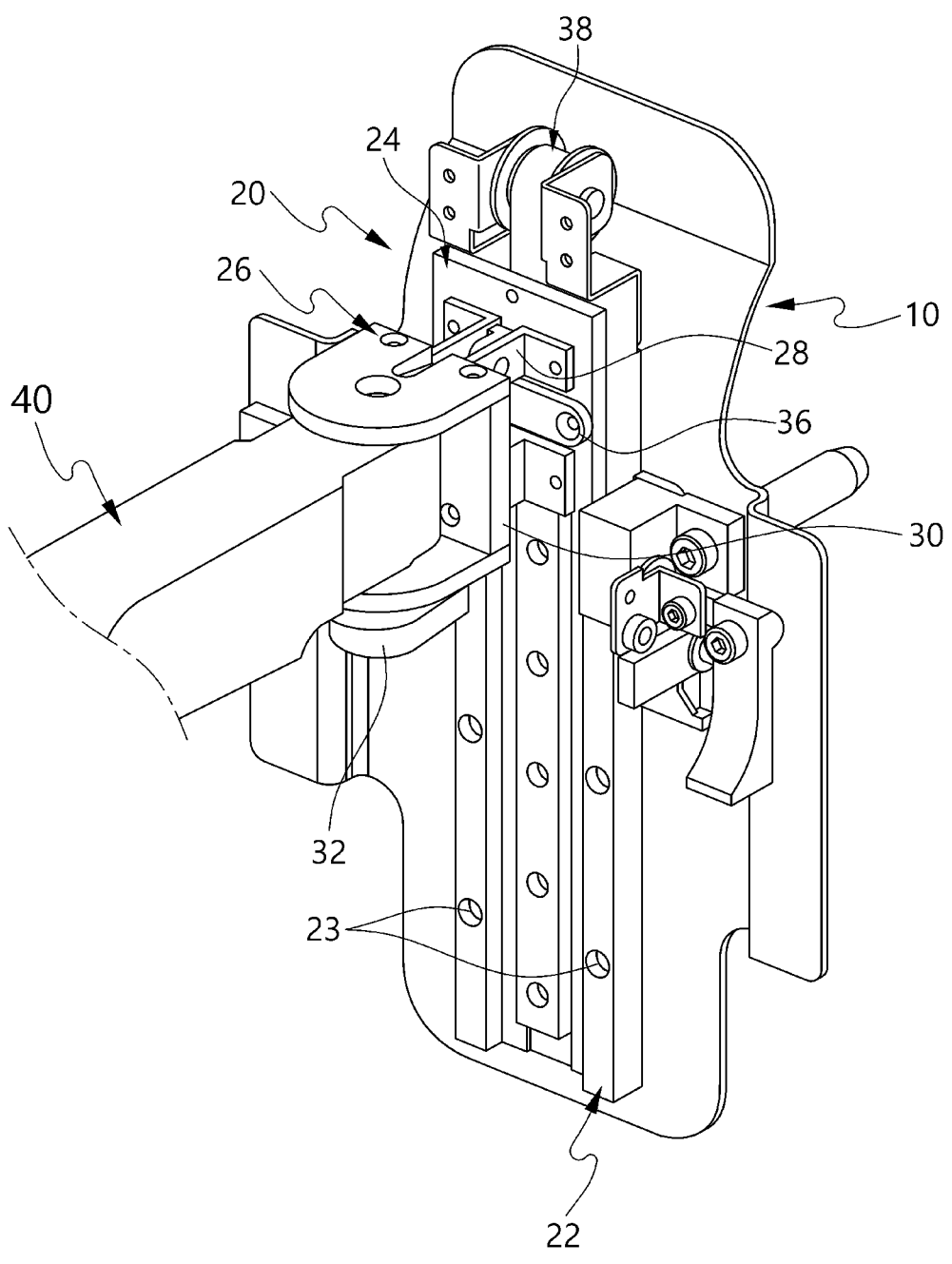
FIG. 8 is a perspective view showing a configuration of an elevation unit of the radiation protection device according to the exemplary embodiment of the present invention.
Figure 9:
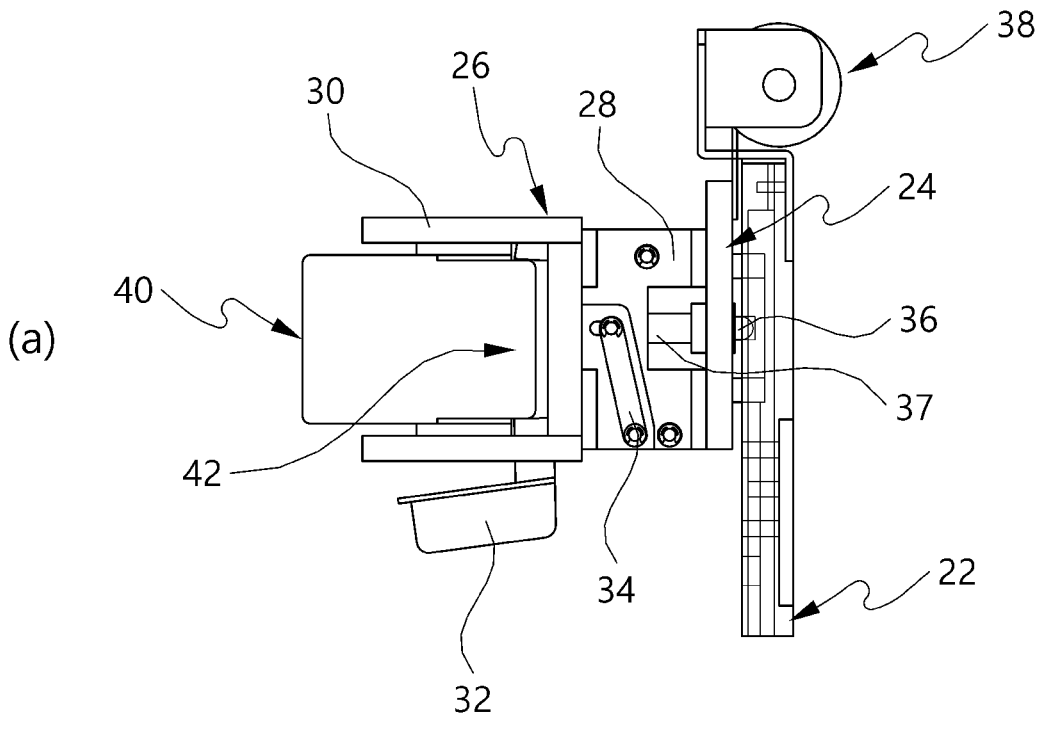
FIG. 9 is a side view showing an actuating state of the elevation unit of the radiation protection device according to the exemplary embodiment of the present invention.
Figure 9:
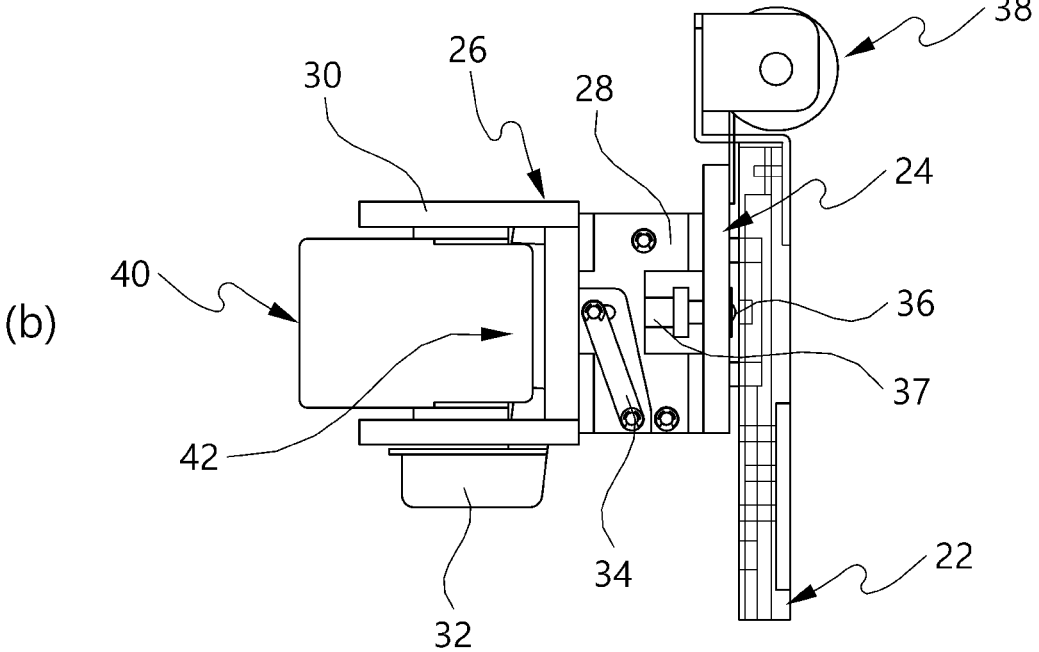

FIG. 8 is a perspective view showing a configuration of an elevation unit of the radiation protection device according to the exemplary embodiment of the present invention, and FIG. 9 is a side view showing an actuating state of the elevation unit of the radiation protection device according to the exemplary embodiment of the present invention.

The elevation unit 20 of the radiation protection device 7 may include a guide part 22 formed in the z-axis direction, a movable block 24 that may be movable along the guide part 22, a rotation support part 26 coupled on one side surface of the movable block 24, a position fixing pin 36 for fixing the movable block 24 to the guide part 22, and an actuating lever 32 for actuating the position fixing pin 36.

The guide part 22 may be fixed to an inner surface of a frame constituting the fixing unit 10. The guide unit 22 may be provided with a plurality of position fixing holes 23 having different heights in the vertical direction. In an exemplary embodiment of FIG. 8, a pair of position fixing holes 23 are formed at the same height on both sides of the guide part 22. However, in an exemplary embodiment of the present invention, only one position fixing hole 23 may be provided at a predetermined height, and a plurality of position fixing holes 23 may be formed at predetermined intervals in the vertical direction. The movable block 24 may be moved in the vertical direction along the guide part 22.

The rotation support part 26 may include a support bracket 30 that rotatably supports a rotation part 42 formed at an end portion of the connecting unit 40, and a mounting bracket 28 fixed to the movable block 24. The position fixing pin 36 and the actuating lever 32 may be provided for the rotation support part 26. The position fixing pin 36 is configured to be movable in a horizontal direction, and the position fixing pin 36 is pressed toward the guide part 22 by a position fixing spring 37. The position fixing pin 36 is inserted into the position fixing hole 23 formed in the guide part 22, so that the vertical positions of the rotation support part 26 and the movable block 24 may be fixed.

The actuating lever 32 serves to move the position fixing pin 36 so that the position fixing pin 36 can be separated from the position fixing hole 23. In an exemplary embodiment, one end portion of the actuating lever 32 may be connected to the position fixing pin 36 by a link member 34. When the actuating lever 32 is actuated by connection through the link member 34, the position fixing pin 36 is separated from the position fixing hole 23, and the movable block 24 can be moved up and down along the guide part 22. The actuating lever 32 may be provided in the form of being pressed from bottom to top. This allows a user to actuate the actuating lever 32 in the manner of supporting the lever from below by a hand to support the weight while releasing the position fixing of the movable block 24, thereby improving actuation stability.

A static load spring 38 coupled with the movable block 24 may be provided in order to prevent a sudden drop due to the load of the elevation unit 20, the connecting unit 40, and the shielding unit 70 in a state in which the position fixing pin 36 is separated from the position fixing hole 23. The static load spring 38 may be provided in the form of being coupled to an upper end of the guide part 22 or coupled to the frame of the fixing unit 10.

Part (a) of FIG. 9 shows a state in which the position fixing pin 36 is inserted in the position fixing hole 23, where the movable block 24 and the rotation support part 26 are maintained in a state of being fixed in positions in the vertical direction. Part (b) of FIG. 9 shows a state in which the position fixing pin 36 is separated from the position fixing hole 23 by actuating the actuating lever 32, where the movable block 24 and the rotation support part 26 are in a state in which they can be movable in the vertical direction.

On the other hand, as shown in FIG. 2, in a state in which the connecting unit 40 and the shielding unit 70 are rotated laterally to the arm unit 2, if the actuating lever 32 is actuated by mistake, and accordingly, the elevation unit 20, the rotation part 42, the shielding unit 70 and the like of the radiation protection device 7 fall, there is a possibility of injuring the patient's arm or the like. In order to prevent this, the radiation protection device 7 may be provided with a configuration for preventing an actuation of the actuating lever 32 when the connecting unit 40 or the like is rotated laterally to the arm unit 2.

Part (a) of FIG. 10 is a view showing a rotation part provided for a connecting unit of the radiation protection device and an actuating lever of the elevation unit in a state of FIG. 1, and part (b) of FIG. 10 is a view showing the rotation part provided for the connecting unit of the radiation protection device and the actuating lever of the elevation unit in a state of FIG. 2.

The rotation part 42 of the connecting unit 40 rotatably supported by the support bracket of the rotation support part 26 is formed with a slot 43, and a link connecting part 33 of the actuating lever 32 connected to the link member 34 is provided in the form of being inserted into the slot 43. Referring to part (a) of FIG. 10, in the state of FIG. 1, an actuation of the actuating lever 32 is permitted while a portion of the link connecting unit 33 of the actuating lever 32 is inserted into the slot 43. Accordingly, the position fixing pin 36 can be separated from the position fixing hole 23. However, referring to part (b) of FIG. 10, in the state of FIG. 2, the upper end of the actuating lever 32 is blocked by the lower surface of the rotation part 42, and therefore, the operation of the actuating lever 32 is blocked, so that the position fixing pin 36 cannot be separated from the position fixing hole 23. That is, a mechanical anti-lock structure for the actuating lever 32 may be provided by the slot 43 formed in the rotation part 42 of the connecting unit 40.

Meanwhile, the rotation part 42 may be further provided with a shaft insertion hole 44 into which a shaft for rotation is inserted. The shaft insertion hole 44 will be further described below.

Next, the detailed configuration of the connecting unit 40 will be described.

FIG. 11 is a cross-sectional view showing a detailed configuration of the connecting unit connected to a rotation support part of the radiation protection device according to the exemplary embodiment of the present invention, and FIG. 12 is a perspective view of a fixing shaft provided for the rotation support part of the radiation protection device according to the exemplary embodiment of the present invention. In addition, FIG. 13 is a view showing a height at which rotation of the connecting unit of the radiation protection device according to the exemplary embodiment of the present invention can be enabled.

In an exemplary embodiment, the connecting unit 40 includes a connecting unit frame 46, a rotation part 42 provided at one end portion of the connecting unit frame 46, a rotation fixing part 48 provided in the connecting unit frame 46, and an unfixing operation part 54 for releasing a fixed state of the rotation fixing part 48.

Referring to FIGS. 11 and 12, the support bracket 30 of the rotation support part 26 is provided with a fixing shaft 56 forming a rotation axis of the rotation part 42 of the connecting unit 40. The fixing shaft 56 is fixed in the support bracket 30, and at least one fixing groove 57 is provided on an outer circumferential surface of the fixing shaft 56. In an exemplary embodiment, a plurality of fixing grooves 57 may be provided at intervals of a predetermined angle (e.g., 90 degrees, 70 degrees, or 45 degrees) along a circumferential direction.

The rotation fixing part 48 provided inside the connecting unit frame 46 of the connecting unit 40 includes a rotation fixing pin 50 elastically supported by a rotation fixing spring 51 and having one end portion inserted into the fixing groove 57 of the fixing shaft 56, and a rotation fixing pin driving link 52 for retracting the rotation fixing pin 50. In an exemplary embodiment, the rotation fixing pin driving link 52 may be configured in the form of a two-bar link, and the rotation fixing pin 50 may be connected to an end portion thereof.

The unfixing operation part 54 may be exposed to the outside and provided in the form of a button so that the user can operate it. When the unfixing operation part 54 is pressed, the rotation fixing pin driving link 52 is actuated, so that the rotation fixing pin 50 retreats away from the fixing shaft 56.

In a state in which the end portion of the rotation fixing pin 50 is inserted into the fixing groove 57 by the rotation fixing spring 51, the connecting unit 40 cannot rotate with respect to the rotation support part 26. When the unfixing operation part 54 is operated to actuate the rotation fixing pin driving link 52, the rotation fixing pin 50 connected to the rotation fixing pin driving link 52 retreats and separates from the fixing groove 57 of the fixing shaft 56. Accordingly, the rotation restriction of the connecting unit 40 with respect to the rotation support part 26 is released, so that the connecting unit 40 can be rotated.

In an exemplary embodiment of the present invention, the height at which left and right rotation of the connecting unit 40 and the shielding unit 70 can be enabled may be limited.

Referring to FIGS. 11 and 13, the rotation support part 26 may be provided with a locking piece 60. In addition, the fixing unit 10 of the radiation protection device 7 may be provided with a locking piece release part 58. The locking piece 60 may be provided to be rotatable about a locking piece rotation shaft 66, a locking part 62 may be formed on one side of the locking piece rotation shaft 66, and a contact part 64 may be provided on the other side of the locking piece rotation shaft 66. The locking piece release part 58 may be formed with a pressing portion 59 that can come into contact with the contact part 64.

In an exemplary embodiment, the locking part 62 of the locking piece 60 may be inserted into an upper side of the slot 43 provided in the rotation part 42 of the connecting unit 40 (part (a) of FIG. 13). In a state where the locking part 62 of the locking piece 60 is inserted into the slot 43 of the rotation part 42, the connecting unit 40 is not rotated even when the rotation fixing pin 50 is separated from the fixing groove 57 by operating the unfixing operation part 54. When the elevation unit 20 is moved up and the contact part 64 of the locking piece 60 is thus pressed by the locking piece release part 58 (part (b) of FIG. 13), the locking part 62 of the locking piece 60 is separated from the slot 43 and the rotation of the connecting unit 40 can be enabled.

With such a configuration, the connecting unit 40 and the shielding unit 70 can be rotated in a state in which the heights thereof are raised to predetermined positions, and therefore, the collision with the patient or other equipment due to the rotations of the connecting unit 40 and the shielding unit 70 can be prevented.

Although the technical idea of the present invention has been described for illustrative purposes with reference to the above embodiment, one skilled in the art will appreciate that various modifications, changes and substitutions can be made without departing from the scope and spirit of the present invention as disclosed in the accompanying claims. Therefore, the embodiments and accompanying drawings of the present invention are presented only for illustrative purposes, not for limiting the technical idea of the present invention, and the scope of the technical idea of the present invention is not limited by the embodiments and accompanying drawings. The protection scope of the present invention should be construed according to the following claims, and all technical ideas within the equivalent range should be construed as being included in the scope of the present invention.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A radiation protection device provided for a radiographic imaging apparatus, the radiation protection device comprising:
   a fixing portion fixed to an arm portion of the radiographic imaging apparatus;
   an elevation portion coupled to the fixing portion to be movable along a first direction;
   a connector coupled to the elevation portion to be rotatable in a second direction different from the first direction; and
   a shielding portion provided on one side of the connector to shield radiation,
   wherein the connector comprises a connector frame, a rotation part provided on one side of the connector frame and coupled to a rotation support part of the elevation portion, and a rotation fixing part provided on the connector frame and configured to selectively enable rotation of the rotation part with respect to the rotation support part.

2. The radiation protection device of claim 1, wherein the fixing portion comprises a fixing pin and a fixing hook protruding from a rear surface of the fixing portion, and the fixing hook is configured to fix the fixing portion to the arm portion by being hooked on an engaging part provided inside the arm portion.

3. The radiation protection device of claim 2, wherein the fixing portion comprises a disengaging operation part configured to rotate the fixing hook to release an engaged state of the fixing hook.

4. The radiation protection device of claim 1, wherein the rotation support part is provided with a fixing shaft having a fixing groove defined on an outer circumferential surface thereof,
   wherein the rotation part is coupled to the rotation support part by using the fixing shaft as a rotation axis, and
   wherein the rotation fixing part comprises a rotation fixing pin configured to block the rotation of the rotation part by being inserted into the fixing groove.

5. The radiation protection device of claim 4, wherein the rotation fixing pin is configured to be pressed toward the fixing groove by a rotation fixing spring, and
   wherein the connector comprises an unfixing operation part configured to be operated to separate the rotation fixing pin from the fixing groove.

6. The radiation protection device of claim 5, wherein the connector frame is provided with a rotation fixing pin driving link configured to retract the rotation fixing pin by an operation of the unfixing operation part.

7. The radiation protection device of claim 1, wherein rotation of the connector with respect to the elevation portion is allowed when the elevation portion is positioned at a predetermined height in the first direction.

8. The radiation protection device of claim 1, wherein the rotation part of the connector is provided with a slot, and wherein the radiation protection device further comprises a locking piece configured to prevent rotation of the connector in the second direction by being partially inserted into the slot, and to release an inserted state into the slot by a locking piece release part at a predetermined height.

9. A radiographic imaging apparatus, comprising:
a radiation protection device; and
an arm portion to which the radiation protection device is mounted,
wherein the radiation protection device comprises:
a fixing portion fixed to the arm portion of the radiographic imaging apparatus;
an elevation portion coupled to the fixing portion to be movable along a first direction;
a connector coupled to the elevation portion to be rotatable in a second direction different from the first direction; and
a shielding portion provided on one side of the connector to shield radiation, and
wherein the connector comprises a connector frame, a rotation part provided on one side of the connector frame and coupled to a rotation support part of the elevation portion, and a rotation fixing part provided on the connector frame and configured to selectively enable rotation of the rotation part with respect to the rotation support part.

10. The radiographic imaging apparatus of claim 9, wherein the fixing portion comprises a fixing pin and a fixing hook protruding from a rear surface of the fixing portion, and the fixing hook is configured to fix the fixing portion to the arm portion by being hooked on an engaging part provided inside the arm portion.

11. The radiographic imaging apparatus of claim 9, wherein rotation of the connector with respect to the elevation portion is allowed when the elevation portion is positioned at a predetermined height in the first direction.

12. A radiographic imaging apparatus, comprising:
a radiation protection device; and
an arm portion to which the radiation protection device is mounted,
wherein the radiation protection device comprises:
a fixing portion fixed to the arm portion of the radiographic imaging apparatus;
an elevation portion coupled to the fixing portion to be movable along a first direction;
a connector coupled to the elevation portion to be rotatable in a second direction different from the first direction; and
a shielding portion provided on one side of the connector to shield radiation, and
wherein the elevation portion comprises a guide part fixed to the fixing portion, a movable block configured to be movable along the guide part, and a rotation support part provided on one side surface of the movable block and configured to rotatably support the connector.

13. A radiographic imaging apparatus, comprising:
a radiation protection device; and an arm portion to which the radiation protection device is mounted,
wherein the radiation protection device comprises:
a fixing portion fixed to the arm portion of the radiographic imaging apparatus;
an elevation portion coupled to the fixing portion to be movable along a first direction;
a connector coupled to the elevation portion to be rotatable in a second direction different from the first direction; and
a shielding portion provided on one side of the connector to shield radiation, and
wherein the connector comprises a connector frame, a rotation part provided on one side of the connector frame and coupled to a rotation support part of the elevation portion, and a rotation fixing part provided on the connector frame and configured to selectively enable rotation of the rotation part with respect to the rotation support part.

14. A radiation protection device provided for a radiographic imaging apparatus, the radiation protection device comprising:
a fixing portion fixed to an arm portion of the radiographic imaging apparatus;
an elevation portion coupled to the fixing portion to be movable along a first direction;
a connector coupled to the elevation portion to be rotatable in a second direction different from the first direction; and
a shielding portion provided on one side of the connector to shield radiation,
wherein the elevation portion comprises a guide part fixed to the fixing portion, a movable block configured to be movable along the guide part, and a rotation support part provided on one side surface of the movable block and configured to rotatably support the connector.

15. The radiation protection device of claim 14, wherein the guide part has a plurality of position fixing holes defined at different heights along the first direction, and
wherein the movable block or the rotation support part has a position fixing pin configured to be inserted into one of the plurality of position fixing holes to fix a position.

16. The radiation protection device of claim 15, wherein the position fixing pin is configured to be pressed toward the plurality of position fixing holes by a position fixing spring, and
wherein the elevation portion further comprises an actuating lever to separate the position fixing pin from the one of the plurality of position fixing holes.

17. The radiation protection device of claim 16, wherein a rotation part of the connector rotatably coupled to the rotation support part is defined with a slot, and an actuation of the actuating lever is allowed only in a state in which the slot is aligned with the actuating lever.

18. The radiation protection device of claim 14, wherein the elevation portion further comprises a static load spring to support the movable block from an upper side.

* * * * *